United States Patent
Saloma et al.

(10) Patent No.: US 7,235,988 B2
(45) Date of Patent: Jun. 26, 2007

(54) METHOD FOR GENERATING HIGH-CONTRAST IMAGES OF SEMICONDUCTOR SITES VIA ONE-PHOTON OPTICAL BEAM-INDUCED CURRENT IMAGING AND CONFOCAL REFLECTANCE MICROSCOPY

(75) Inventors: Caesar A. Saloma, National Institute of Physics, College of Science, University of the Philippines Diliman, Quezon City (PH) 1101; Jelda Jayne C. Miranda, National Institute of Physics, College of Science, University of the Philippines Diliman, Quezon City (PH) 1101; Vincent Ricardo M. Daria, National Institute of Physics, College of Science, University of the Philippines Diliman, Quezon City (PH) 1101

(73) Assignees: Caesar A. Saloma (PH); Vincent Ricardo M. Daria (PH); Jelda Jayne C. Miranda (PH)

(*) Notice: Subject to any disclaimer, the term of this patent is extended or adjusted under 35 U.S.C. 154(b) by 0 days.

(21) Appl. No.: 10/520,729

(22) PCT Filed: Jul. 9, 2002

(86) PCT No.: PCT/PH02/00013

§ 371 (c)(1),
(2), (4) Date: Dec. 9, 2005

(87) PCT Pub. No.: WO2004/008164

PCT Pub. Date: Jan. 22, 2004

(65) Prior Publication Data

US 2006/0165272 A1    Jul. 27, 2006

(51) Int. Cl.
*G01R 31/308* (2006.01)

(52) U.S. Cl. ............ 324/753; 324/750; 324/751; 359/385; 359/368

(58) Field of Classification Search .......... None
See application file for complete search history.

(56) References Cited

U.S. PATENT DOCUMENTS

| | | | |
|---|---|---|---|
| 5,381,224 A | 1/1995 | Dixon et al. | 356/72 |
| 6,316,950 B1 * | 11/2001 | Denk et al. | 324/752 |
| 6,549,022 B1 * | 4/2003 | Cole et al. | 324/752 |

FOREIGN PATENT DOCUMENTS

| | | |
|---|---|---|
| DE | 19733194 | 2/1999 |
| JP | 2000088929 | 3/2000 |

OTHER PUBLICATIONS

Notication of Transmittal of the International Search Report or The Declaration dated Mar. 26, 2003 from PCT/PH02/00013.

(Continued)

*Primary Examiner*—Minh N. Tang
(74) *Attorney, Agent, or Firm*—Ohlandt, Greeley, Ruggiero & Perle L.L.P.

(57) ABSTRACT

A method is disclosed that permits the generation of exclusive high-contrast images of semiconductor sites in an integrated circuit sample (19). It utilizes the one-photon optical beam-induced current (1P-OBIC) image and confocal reflectance image of the sample that are generated simultaneously from one and the same excitation (probe) light beam that is focused on the sample (19). A 1P-OBIC image is a two-dimensional map of the currents induced by the beam as it is scanned across the circuit surface. 1P-OBIC is produced by an illuminated semiconductor material if the excitation photon energy exceeds the bandgap. The 1P-OBIC image has no vertical resolution because 1P-OBIC is linear with the excitation beam intensity. The exclusive high-contrast image of semiconductor sites is generated by the product of the 1P-OBIC image and the confocal image. High-contrast image of the metal sites are also obtained by the product of the complementary OBIC image and the same confocal image.

10 Claims, 3 Drawing Sheets

OTHER PUBLICATIONS

Montangero et al. "A Som Approach to The Failure Physics of Optoelectronic Devices", Proceedings of the International Reliability Physics Symposium. Atlanta, Mar. 23-25, 1993. New York, IEEE, US, vol. SYMP. 31 Mar. 23, 1993, pp. 380-385.

Nikawa et al. "Failure Analysis Case Studies Using the IR-OBIRCH (Infared Optical beam Induced Resistance Change Method", Test Syposium Proceedings, Eighth Asian Shanghai, China Nov. 16-18, 1999, Los Alamitos, CA, IEEE Comput. Soc, US Nov. 16, 1999. pp. 394-399.

Ribes et al. "Reflected-light, photoluminescence and OBIC imaging Of solar cells using a confocal scanning laser MACROscope/microscope". Solar Energy Materials and Solar Cells 44, Dec. 15, 1996. pp. 439-350.

Xu et al. "Comparison of one- and two-photon optical beam-induced current imaging". Journal of Applied Physics. vol. 86 No. 4, Aug. 15, 1999. pp. 2226-2231.

* cited by examiner

METHOD FOR GENERATING HIGH-CONTRAST IMAGES OF SEMICONDUCTOR SITES VIA ONE-PHOTON OPTICAL BEAM-INDUCED CURRENT IMAGING AND CONFOCAL REFLECTANCE MICROSCOPY

CROSS-REFERENCE TO RELATED APPLICATIONS

The present application is a U.S. national stage entry under 35 U.S.C. 371, of International Application No. PCT/PH2002/000013, filed Jul. 9, 2002.

FIELD OF THE INVENTION

The invention relates to a method of precisely determining the location of defects in an integrated circuit.

BACKGROUND OF THE INVENTION

Optical beam induced current (OBIC) imaging is widely employed for failure or defect detection of pn junctions, inter-level shorts, transistor states, etc, in integrated circuits (IC). An OBIC image is a map of the current magnitudes that are induced when a (focused) optical beam is scanned across an IC sample. Scanning confocal microscopy with its focused probe beam, is readily combined with OBIC imaging to produce a pair of confocal reflectance- and OBIC images of the sample from one and the same beam scan.

The one-photon absorption OBIC (1P-OBIC) is produced by an illuminated semiconductor material if the probe photon energy exceeds the semiconductor bandgap $E_b$ i.e. $\lambda_p \leq hc/E_b$, where $\lambda_p$ is single-photon wavelength, h is the Planck's constant and c is the speed of light in vacuum. 1P-OBIC is proportional to the probe beam intensity and the measured 1P-OBIC signal is an integrated effect along the optical beam path. Unlike confocal images which are high-contrast displays of the reflectance of a three-dimensional sample, the corresponding 1P-OBIC image of the same sample has low contrast and lacks vertical resolution.

Two-photon OBIC (2P-OBIC) has been demonstrated to generate high-contrast images of semiconductor sites in an IC. 2P-OBIC utilizes an excitation beam with a wavelength $\lambda_{2P} > hc/E_b$. 2P-OBIC is proportional to the square of the beam intensity and is highly localized within the focal volume of the excitation beam. Another technique for obtaining high-contrast 1P-OBIC images is via near-field microscopy with a subwavelength fiber Up. A major drawback of 2P-OBIC is the high cost of a femtosecond laser source. Image generation in near-field microscopy is slow and unsuitable for generating large image fields. It is also sensitive to ambient experimental conditions.

Here, we present a procedure for generating high-contrast images of semiconductor sites in the IC from their 1P-OBIC image and confocal reflectance image which are both obtained from the same focused beam. The procedure utilizes the following properties: (1) only semiconductor materials produce an OBIC signal, and (2) confocal reflectance images are optically-sectioned images of both metallic and semiconductor surfaces. We show that the product of the low-contrast 1P-OBIC image and the confocal image results in a high-contrast (axial-dependent) map that reveals only the semiconductor sites in the confocal image. Similarly, the product of the complementary to the 1P-OBIC image and the confocal image yields an optically sectioned image exclusively of the non-semiconductor sites in the IC sample.

Another advantage of 2P-OBIC imaging over 1P-OBIC is realized when observing in the presence of an intervening highly scattering medium between the focusing lens and the semiconductor material. Because the scattered intensity is inversely proportional to a power of the incident wavelength and that $\lambda_{2P}=2\lambda_p$, a much greater percentage of the 2P excitation photons is delivered at the focal volume of a 2P excitation beam than their 1P counterparts for the same scattering medium and numerical aperture (NA) of the focusing lens. The scatter-induced broadening of the axial distribution of the 2P-OBIC signal is less severe than that of 1P-OBIC. In 1P fluorescence excitation microscopy with large-area photodetector, the effect of scattering is to degrade the signal-to-noise ratio of the generated images.

It is worth noting that confocal microscopy is also robust against the unwanted effects of scattering by an intervening medium. The photodetector pinhole acts a spatial filter that permits only the detection of photons emanating from the focal volume of the probe beam. The undesirable image contribution of the photons from the out-of-focus planes can be minimized through careful choice of the pinhole size.

1P excitation (1PE) confocal microscopy can be done with objectives of relatively low NA values but long working distances—an advantage that is of practical importance for wide-field observation and when dealing with thick samples. In contrast, 2PE imaging requires objectives with large NA values to generate sufficiently high intensities at the focal spot because the 2PE absorption cross-section is much smaller than its 1PE counterpart. Such objectives however, normally have short working distances that limit our ability to scan axially thick samples at long depths. Aberration-free high NA objectives with long working distances are quite expensive to manufacture.

SUMMARY OF THE INVENTION

The present invention, in one broad sense, is about the discovery that exclusive high-contrast images of semiconductor sites can be generated quickly and accurately from the 1P-OBIC image and the confocal reflectance image which are obtained via one and the same excitation beam that is focused on the IC sample.

The process makes use of the fact that: (1) confocal images are optically-sectioned images while 1P-OBIC images are exclusive low-contrast images of semiconductor sites, and (2) both the confocal image and 1P-OBIC image are produced with an optical beam.

BRIEF DESCRIPTION OF THE DRAWINGS

The detailed description of the invention can be readily appreciated in conjunction with the accompanying drawings, in which.

DETAILED DESCRIPTION OF THE INVENTION

Figure 1:
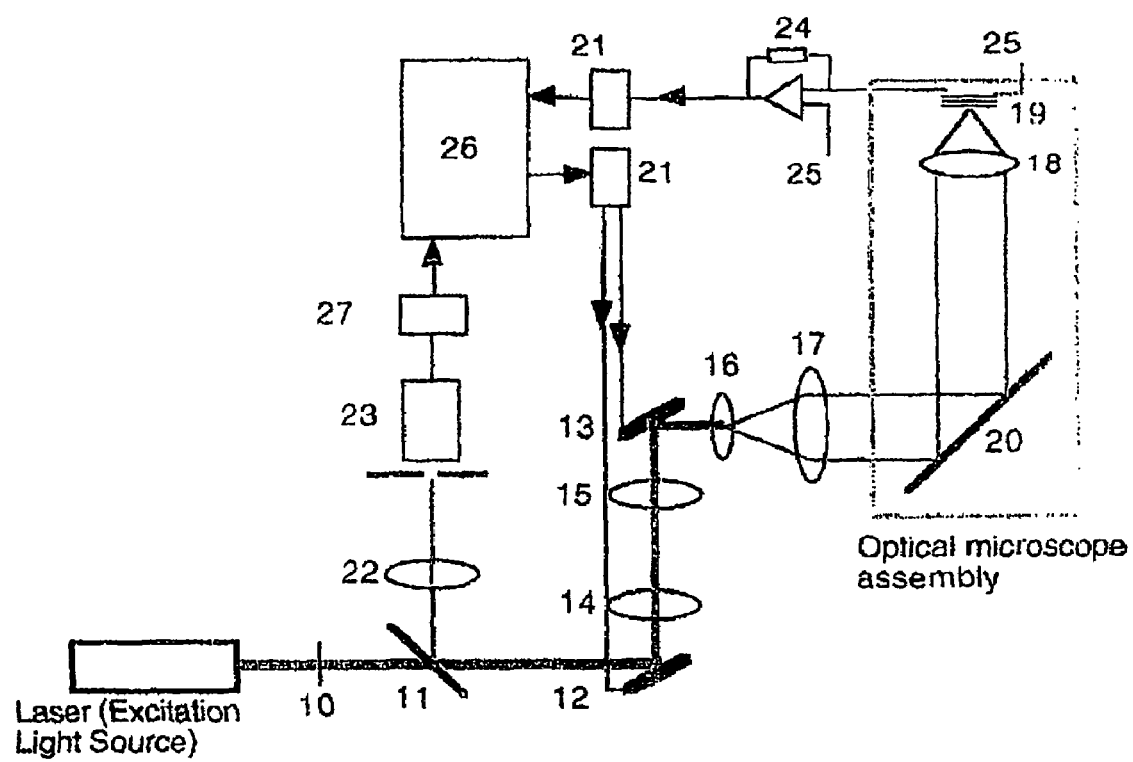
FIG. 1 is an optical set-up of beam-scanning optical microscope for simultaneous confocal reflectance and 1P-OBIC imaging. The optical excitation power is controlled via a neutral density filter (10).
Figure 2:
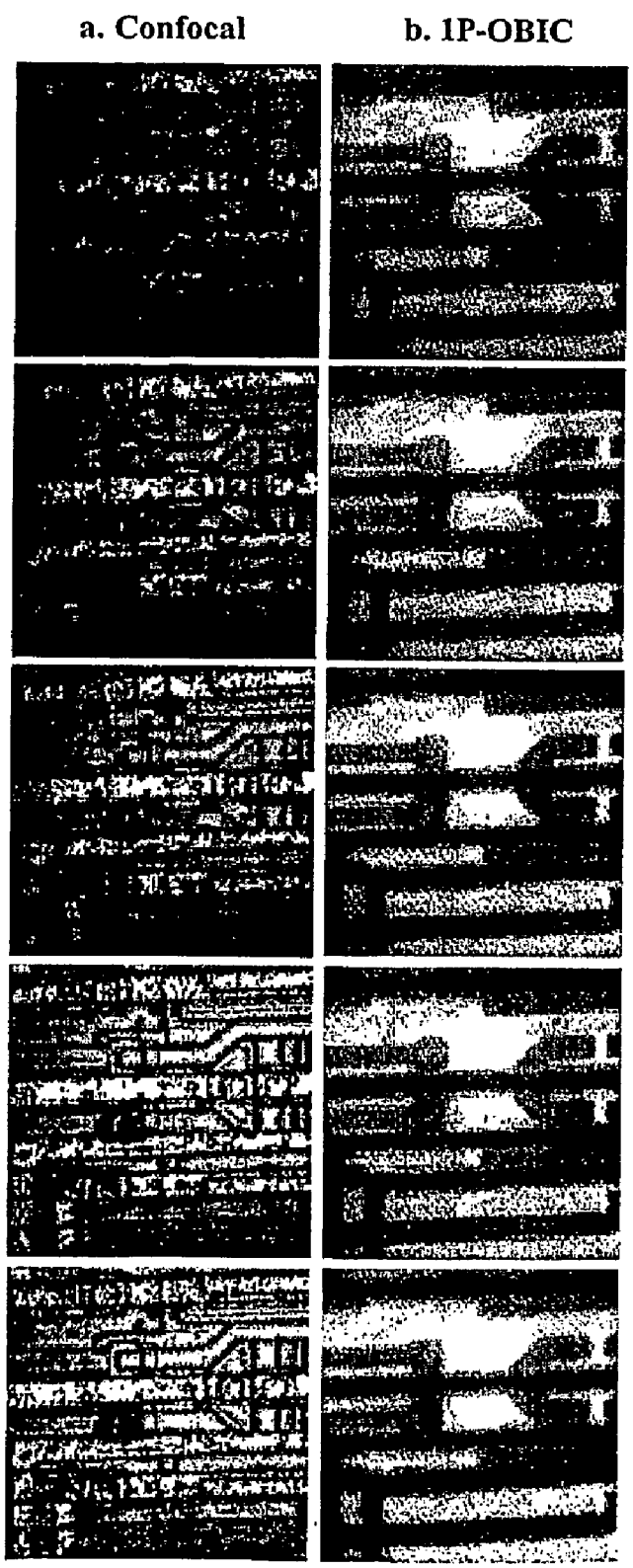
FIG. 2 presents a comparison of confocal (a) and 1P-OBIC (b) images at various axial locations ($\Delta z=1$ micron, 128 by 128 pixels, and image size: 30 micron×30 micron). The images are (raw) outputs of the optical set-up described in FIG. 1.
Figure 3:
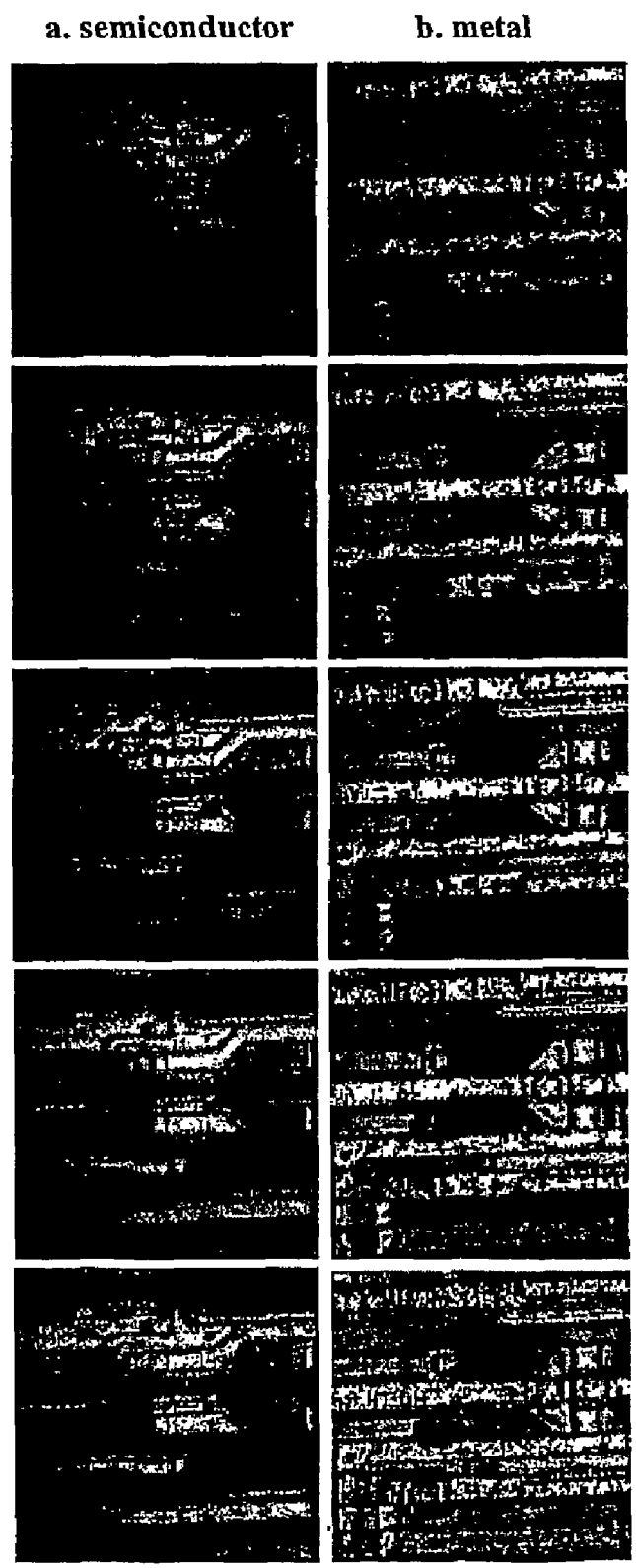
FIG. 3 shows the exclusive images of semiconductor sites (a) and metal sites (b) at various axial locations ($\Delta z=1$ micron, 128 by 128 pixels, and image size: 30 micron×30 micron). The images are derived using the confocal and 1P-OBIC images in FIG. 2.

The teachings of the present invention can be readily understood with reference to the accompanying figures, in which details of the preferred manner of practicing the present art are described. Accordingly, persons of skill in the appropriate arts may modify the disclosures of the present invention but still obtain the favorable results described herein. Since the understanding of the underlying principles about optical image formation are key to the process, a description of the same is in order.

Underlying Principle

The amplitude point spread function (PSF) of a confocal microscope (with a point light source and a point detector) is given by: $h_1(x, y, z)h_2(x, y, z)=h_1h_2$, where $h_1$ and $h_2$ are the point spread function of the focusing and collector lens, respectively. In a confocal reflectance microscope, $h_1=h_2=h$. The confocal intensity image $i_r(x, y, z)$ that is generated from a three-dimensional object with a reflection amplitude distribution $o_r(x, y, z)$ is described by:

$$i_r(x, y, z) = |o_r(x, y, z)h^2(x, y, z)|^2 \quad (1)$$

where represents a convolution operation. Metals and semiconductors surfaces have relatively high $|o_r(x, y, z)|^2$ values. The intensity PSF which is the confocal image that is produced by a point object is: $|h^2(x, y, z)|^2$. The optical sectioning capability of a confocal microscope that permits the generation of high-contrast images is a consequence of the $|h^2(x, y, z)|^2$-behavior of the PSF.

The same focused beam of the confocal microscope generates the 1P-OBIC signal whose strength is proportional to the beam intensity and depends not only on the 1P absorption cross-section and the incident beam power but also on the optical path length. This implies that the measured 1P-OBIC signal $i_s$ does not exhibit a z-dependence and is calculated as:

$$i_s(x, y) = \int_{-\infty}^{\infty} o_s(x, y, z,) \otimes |h(x, y, z)|^2 \, dz \quad (2)$$

where $o_s(x, y, z)$ represents the distribution of the semiconductor material in the sample and $i_s(x, y) \geq 0$. For non-semiconductor materials (e.g. metals, dielectrics), $o_s(x, y, z)=0$. Because $i_s(x, y)$ has no axial dependence, a 1P-OBIC image has low contrast and contains no information about the depth distribution of the semiconductor sites in the sample. It has already been reported earlier that the 1P-OBIC image lacks vertical resolution.

However, an exclusive high-contrast image of semiconductor sites can be derived from $i_r(x, y, z)$ and $i_s(x, y)$ by taking their image product: $s(x, y, z)=i_r(x, y, z)i_s(x, y)$, where $s(x, y, z) \geq 0$. From the properties of $o_r(x, y, z)$ and $o_s(x, y, z)$, it is evident that $s(x, y, z)$ is non-zero only for semiconductor materials. From Eqs (1) and (2), the associated PSF for the product image is given by: $h^4(x, y, z) \int h^2(x, y, z)dz = h^6(x, y)h^4(z)$, where we have assumed that: $h(x, y, z)=h(x, y)h(z)$, in the final expression. Therefore, $s(x, y, z)$ provides an exclusive map of the semiconductor sites and exhibits the vertical resolution of $i_r(x, y, z)$.

An exclusive high-contrast image of the metallic sites is obtained from the product: $m(x, y, z)=i_r(x, y, z)i_m(x, y)$, where: $i_m(x, y)=\kappa-i_s(x, y)$, and $\kappa$ is a constant that represents the highest $s(x, y, z)$ value that is possible for a given optical set-up. In practice, the sample is scanned by the focused beam at a sampling interval that takes into account the central spot size of $h(x, y, z)$ and the Rayleigh resolution criterion. The scanned confocal and 1P-OBIC images are represented by $\{i_r(i, j, k)\}$ and $\{i_s(i, j, k)\}$ respectively, where: $x=i\Delta x$, $y=j\Delta y$, and $z=k\Delta z$, $i, j=1, 2, \ldots J$; and $k=1, 2, \ldots, K$. The sampling intervals are given by $\Delta x$, $\Delta y$, and $\Delta z$, respectively. In our experiments, an 8-bit analog-to-digital converters are utilized for both $i_r(x, y, z)$ and $i_s(x, y)$ so that: $0 \leq i_r(i, j, k) \leq 255$; and $0 \leq i_s(i, j, k) \leq \kappa=255$.

The algorithm for generating each element in scanned product image $\{s(i, j, k)\}=\{i_r(i, j, k)i_s(i, j, k)\}$, has a computational complexity of order 1. It could be implemented very quickly. The $s(i, j, k)$-values are also not susceptible to rounding-off errors which are attendant in iterative reconstruction algorithms with high computational complexity.

Experimental Set-up

A beam-scanning reflectance microscope was constructed for both 1 P-OBIC and confocal imaging (FIG. 1). Via a beam splitter (11), the output beam of laser is directed to a scanning mirror system that is composed of two galvanometer mirrors (General Scanning Model G115) for x (12) and y (13) scanning, and two lenses (L1, L2) (14, 15) that constitute a 4f transfer lens. Another pair of lenses (16, 17) expands and collimates the scanned beam and inputs it to an optical microscope assembly. An infinity-corrected objective lens (18) focuses the beam into the exposed top surface of the integrated circuit sample (19). The beam is directed using a plane mirror (20). Precise 2D scan control of the focused beam is achieved via a pair of digital-to-analog converters (21).

The reflected light is collected back by the same objective lens (18) and focused by lens (22) towards a pinhole that is placed in front of photodetector (23). The 1P-OBIC is measured by inputting the output of the pin that is nearest to the probe surface area to a current-to-voltage converter composed of an operational amplifier and a feedback resistor (24). The other converter input is the common reference (25) for the electronic circuits including the IC sample. A 1P-OBIC signal is induced because the bandgap $E_b$ is less than the excitation photon energy.

The control of the instrument, the data acquisition system and the post-detection processing are implemented via a personal computer (26). Both the 1P-OBIC signal and the photodetector signal are sampled to the computer by a pair of analog-to-digital converters (27).

CONCLUSION

An efficient and economical method has been disclosed that permits the generation of exclusive high-contrast images of semiconductor sites in an integrated circuit sample. It utilized the one-photon optical beam-induced current (1P-OBIC) image and confocal reflectance image of the sample that are generated simultaneously from one and the same excitation (probe) light beam that is focused on the sample. The exclusive high-contrast image of semiconductor sites is generated by the product of the 1P-OBIC image and the confocal image. High-contrast image of the metal sites are also obtained by the product of the complementary OBIC image and the same confocal image.

That which is claimed is:

1. A method of high contrast imaging of semiconductor and metallic sites in an integrated circuit (IC) that simultaneously produces two separate exclusive high-contrast images of said IC from one light source, the method comprising:

exciting said IC with a focused excitation beam from a light source;

transversely and axially scanning said IC by said focused excitation beam;

producing simultaneously a high-contrast confocal reflectance image $i_r(x, y, z)$ and a low contrast one-photon optical beam-induced current image (1P-OBIC) $i_s(x, y)$ of said IC;

deriving a first exclusive high-contrast image $s(x, y, z)$ of said semiconductor sites of said IC from a pixel to pixel product of said 1P-OBIC image and said confocal reflectance image using the equation: $s(x, y, z)=i_r(x, y, z)i_s(x, y)$ where $s(x, y, z)>0$; and deriving a second exclusive high-contrast image $m(x, y, z)$ of said metallic sites of said IC from a product of a complementary to said 1P-OBIC image and said confocal reflectance image using the equation: $m(x, y, z)=i_r(x, y, z)i_m(x, y)$ where $i_m(x, y)=\kappa-i_s(x, y)$ and $\kappa$ is a constant that represents the highest $s(x, y, z)$ value that is possible for a given optical set-up.

2. The method of claim 1, wherein said focused excitation beam is a beam-scanning confocal reflectance microscope.

3. The method of claim 1, wherein said light source is selected from the group consisting of a laser and a spectrally filtered light source with a broadband spectrum.

4. The method of claim 3, wherein said device includes a scanning mirror system having two galvanometer mirrors for x and y scanning, and two lenses that constitute a 4$f$ transfer lens, wherein said light source is directed to said scanning mirror system.

5. The method of claim 4, wherein said device includes another pair of lenses that expand and collimate said excitation beam and inputs said excitation beam to an optical microscope assembly.

6. The method of claim 5, wherein said device includes an Infinity-corrected objective lens that focuses said excitation beam into said IC.

7. The method of claim 6, wherein said device includes a pair of digital-to-analog converters to achieve precise two-dimensional scan control of said focused excitation beam.

8. The method of claim 7, wherein said device provides reflected light that is collected back by said Infinity-corrected objective lens and focused by a lens towards a pinhole that is placed in front of a photodetector.

9. The method of claim 8, wherein said 1P-OBIC is measured by inputting an output of said pinhole that is nearest to a probe surface area to a current-to-voltage converter composed of an operational amplifier and a feedback resistor.

10. The method of claim 9, wherein said device includes another converter input that is a common reference for electronic circuits including said IC.

* * * * *